United States Patent
Mezger et al.

(10) Patent No.: US 9,079,871 B2
(45) Date of Patent: Jul. 14, 2015

(54) PREPARING CYCLOCARBONATE-FUNCTIONALIZED COMPOUNDS

(71) Applicant: BASF S.E., Ludwigshafen (DE)

(72) Inventors: Jochen Mezger, Lautersheim (DE); Burkhard Walther, Garching (DE); Joanna Mecfel-Marczewski, Limburgerhof (DE); Rainer Klopsch, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/368,131

(22) PCT Filed: Nov. 29, 2012

(86) PCT No.: PCT/EP2012/073920
§ 371 (c)(1),
(2) Date: Jun. 23, 2014

(87) PCT Pub. No.: WO2013/098030
PCT Pub. Date: Jul. 4, 2013

(65) Prior Publication Data
US 2014/0378689 A1  Dec. 25, 2014

(30) Foreign Application Priority Data
Dec. 29, 2011  (EP) ..................... 11196033

(51) Int. Cl.
C07D 307/33 (2006.01)
C07D 317/40 (2006.01)
C07D 407/14 (2006.01)
C07D 307/20 (2006.01)
C07D 317/38 (2006.01)

(52) U.S. Cl.
CPC ............ C07D 307/20 (2013.01); C07D 307/33 (2013.01); C07D 317/38 (2013.01); C07D 317/40 (2013.01); C07D 407/14 (2013.01)

(58) Field of Classification Search
CPC ... C07D 307/33; C07D 317/40; C07D 407/14
See application file for complete search history.

(56) References Cited

U.S. PATENT DOCUMENTS

| | | | |
|---|---|---|---|
| 4,544,726 A | 10/1985 | Alford et al. | |
| 5,827,928 A | 10/1998 | Morimoto et al. | |
| 6,841,655 B1 | 1/2005 | Gota et al. | |
| 7,968,572 B2 | 6/2011 | Nakai et al. | |
| 8,044,194 B2 | 10/2011 | Dubois et al. | |
| 8,742,137 B2 | 6/2014 | Mecfel-Marczewski et al. | |
| 2010/0317838 A1 | 12/2010 | Dubois et al. | |

(Continued)

FOREIGN PATENT DOCUMENTS

DE  197 37 329 A1  3/1999
EP  0 001 088 A1  3/1979

(Continued)

OTHER PUBLICATIONS

PCT/EP2012/073920—International Search Report, Jan. 2, 2013.
PCT/EP2012/073920—International Written Opinion, Jan. 2, 2013.
PCT/EP2012/073920—International Preliminary Report on Patentability, Jul. 1, 2014.

(Continued)

*Primary Examiner* — Erich A Leeser
(74) *Attorney, Agent, or Firm* — Curatolo Sidoti Co., LPA; Joseph G. Curatolo; Salvatore A. Sidoti

(57) ABSTRACT

An improved process is proposed for preparing cyclocarbonate-functionalized compounds of the general formula (I)

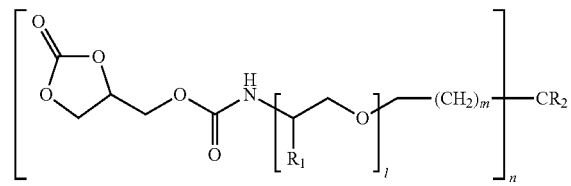

where $R_1$ and $R_2$ in each occurrence are independently selected from hydrogen, methyl and ethyl, l in each occurrence independently is from 2 to 50, m in each occurrence independently is 0 or 1, and n is =3, subject to the proviso that the sum of all l values in the molecule is from 5 to 100, by reacting a chloroformate of formula (II)

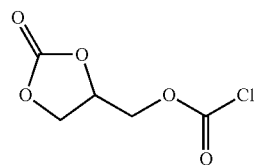

with a trifunctional amine of the general formula (III)

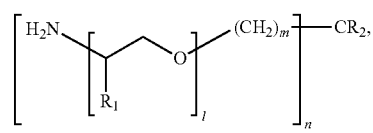

characterized in that the reacting is carried out in an aqueous/organic two-phase system in the presence of an auxiliary base and of a phase transfer catalyst.

7 Claims, No Drawings

(56) References Cited

U.S. PATENT DOCUMENTS

| | | |
|---|---|---|
| 2011/0313177 A1 | 12/2011 | Mecfel-Marczewski et al. |
| 2012/0316286 A1 | 12/2012 | Mecfel-Marczewski et al. |
| 2014/0228583 A1 | 8/2014 | Mecfel-Marczewski et al. |

FOREIGN PATENT DOCUMENTS

| | | | |
|---|---|---|---|
| EP | 0 737 726 A1 | 10/1996 | |
| EP | 1 941 946 A1 | 7/2008 | |
| EP | 2 397 474 A1 | 12/2011 | |
| JP | 7-285960 A | 10/1995 | |
| JP | 09-278982 | 10/1997 | |
| JP | 2003-327854 | 11/2003 | |
| JP | 2006-003433 A | 1/2006 | |
| WO | WO 97/23516 A1 | 7/1997 | |
| WO | WO 2004/003001 A1 | 1/2004 | |
| WO | WO 2007/040208 A1 | 4/2007 | |
| WO | WO 2008/142097 * | 5/2008 | ........... C07D 317/34 |
| WO | WO 2008/142097 A2 | 11/2008 | |
| WO | WO 2011/157551 A1 | 12/2011 | |
| WO | WO 2013/092011 A1 | 6/2013 | |

OTHER PUBLICATIONS

Tomita, et al., "Model Reaction for the Synthesis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science, 2001, vol. 39, pp. 3678-3685, John Wiley & Sons Inc.

Lewis, et al., "Synthesis of L-660,631 Methyl Ester and Related Compounds", Tetrahedron Letters, Jan. 1, 1988, vol. 29, No. 19, pp. 2279-2282, Pergamon Press PLC, Great Britain.

Diakoumakos, Constantino, et al., "Non-Isocyanate-Based Polyurethanes Derived upon the Reaction of Amines with Cyclocarbonate Resins", Macromol. Symp., 2004, vol. 216, pp. 37-46.

Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.

Stevenson, Christian P., et al., "Preparation of (S)-Methyl Glycidate via Hydrolytic Kinetic Resolution", Organic Syntheses, 2006, vol. 83, pp. 162-169; Organic Syntheses Collection, 2009, vol. 11, pp. 157-163.

PCI Paint & Coatings Industry, vol. 29, No. 9, Sep. 2013, pp. 72-73.

* cited by examiner

PREPARING CYCLOCARBONATE-FUNCTIONALIZED COMPOUNDS

CROSS REFERENCE TO RELATED APPLICATIONS

This application is a national stage application of International Application No. PCT/EP2012/073920, filed 29 Nov. 2012, which claims priority from European Patent application No. 11196033.2, filed 29 Dec. 2011, from which applications priority is claimed, and which are incorporated herein by reference.

The present invention relates to an improved process for preparing cyclocarbonate-functionalized compounds of the general formula (I)

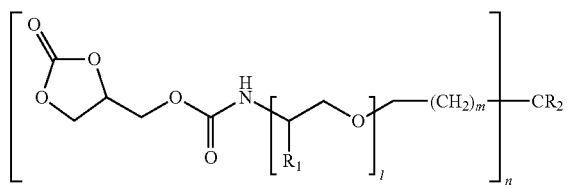
(I)

where $R_1$ and $R_2$ in each occurrence are independently selected from hydrogen, methyl and ethyl, l in each occurrence independently is from 2 to 50, m in each occurrence independently is 0 or 1, and n is =3, subject to the proviso that the sum of all l values in the molecule is from 5 to 100, by reacting a chloroformate of formula (II)

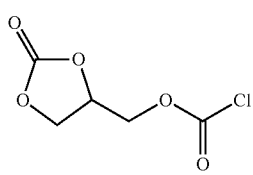
(II)

with a trifunctional amine of the general formula (III)

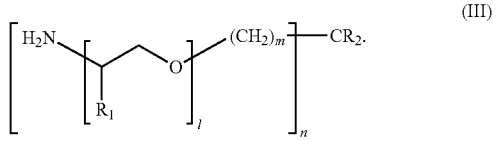
(III)

Two-component systems based on polyisocyanates form part of the state of the art. They are used for example as adhesives, sealants, potting compounds, for corrosion control and for coatings. The high acid, alkali and chemical resistance of the cured compositions thus obtained is advantageous. However, NCO groups are sensitive to moisture. Furthermore, monomeric and low-molecular weight isocyanate compounds are toxicologically concerning, especially when they are volatile or migrate.

Polyurethane systems are also obtainable from cyclic carbonate compounds, which are toxicologically less concerning. For instance, glycerol carbonate (4-(hydroxymethyl)-2-oxo-1,3-dioxolane), which is obtainable from predominantly renewable resources, is used in cosmetics owing to its good compatibility.

Cyclic carbonate compounds react with amines to form hydroxyurethanes. Two different hydroxyurethanes are possible in principle, namely hydroxyurethanes having primary or secondary hydroxyl groups, e.g.:

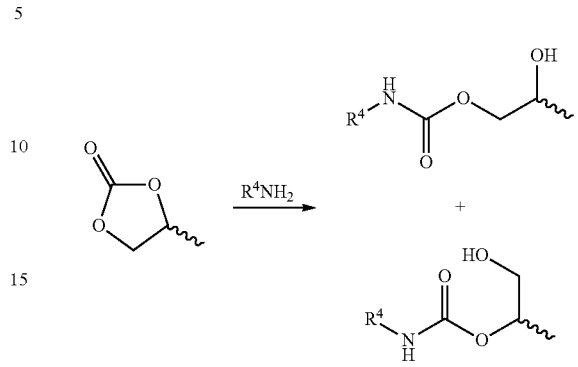

Useful amines here include primary and secondary amines having alkyl groups, aryl groups, aralkyl groups and alkaryl groups. Especially comparatively high molecular weight (poly)amines such as, for example, Jeffamines® from Huntsman Corp. and polyetheramines from BASF SE are of interest here.

However, in order that glycerol carbonate (4-(hydroxymethyl)-2-oxo-1,3-dioxolane) can be used for preparing amine-curable binders, its 4-hydroxymethyl group has to be linked to comparatively high molecular weight di-, tri- or polyfunctional compounds. This can be done via the glycerol carbonate chloroformate of formula (II), which is obtainable as per one of the methods described in DE 19737329 A1.

WO 2008/142097 A2 describes a process for preparing compounds of the general formula (1),

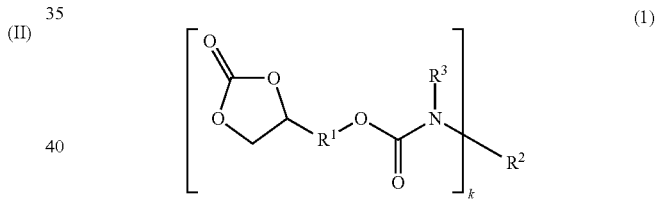
(1)

where $R^1$ is $C_{1-12}$ alkylene, k is 1 or an integer greater than 1 and $R^2$ and $R^3$ are different organic moieties, although when k is an integer greater than 1, $R^2$ is a k-valent aliphatic, cycloaliphatic, aromatic or araliphatic hydrocarbon moiety which optionally contains one or more heteroatoms, by reacting a compound of the general formula (2)

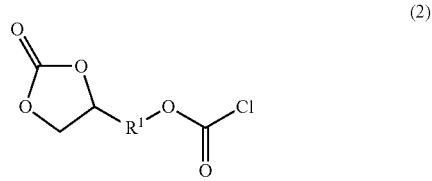
(2)

with an amine of the general formula (3) or a salt thereof,

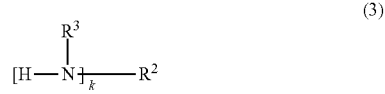
(3)

where $R^1$, $R^2$, $R^3$ and k are each as defined above.

Yet the only cases described in the description and examples of WO 2008/142097 A2 are those where k is =1 or 2. In-house investigations have shown that the yields are relatively poor in cases where k is =3.

The problem addressed by the present invention was that of substantially overcoming at least some of the disadvantages of the prior art. More particularly, an improved synthesis of cyclocarbonate-functionalized compounds of the general formula (I) was to be provided.

This problem is solved by the features of the independent claim. The dependent claims relate to preferred embodiments.

It was found that, surprisingly, the use of an auxiliary base and of a phase transfer catalyst in an aqueous/organic two-phase system leads to an appreciable improvement in the process according to the present invention.

The present invention accordingly provides a process for preparing cyclocarbonate-functionalized compounds of the general formula (I)

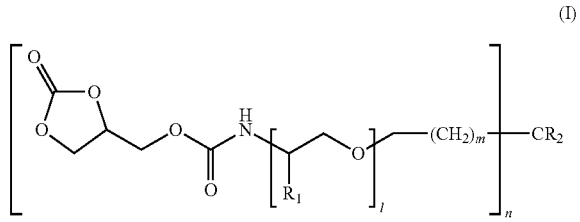

(I)

where $R_1$ and $R_2$ in each occurrence are independently selected from hydrogen, methyl and ethyl, l in each occurrence independently is from 2 to 50, m in each occurrence independently is 0 or 1, and n is =3, subject to the proviso that the sum of all l values in the molecule (i.e. the sum total of all individual indices "l" in the three chains of the molecule) is from 5 to 100, by reacting a chloroformate of formula (II), i.e. (2-oxo-1,3-dioxolan-4-yl)methyl chloroformate,

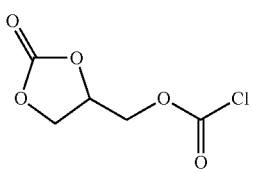

(II)

with a trifunctional amine of the general formula (III)

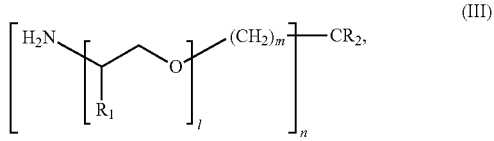

(III)

characterized in that the reacting is carried out in an aqueous/organic two-phase system in the presence of an auxiliary base and of a phase transfer catalyst.

The organic solvent is preferably selected from tetrahydrofuran, diethyl ether, chloroform, methylene chloride and mixtures thereof.

The auxiliary base is preferably selected from sodium bicarbonate, pyridine, triethylamine and mixtures thereof.

The phase transfer catalyst is preferably selected from quaternary ammonium salts and is preferably tetrabutylammonium hydrogensulphate.

It is preferable to use from 0.1% to 10% by weight of phase transfer catalyst, based on the total amount of substance.

The process of the present invention may preferably be carried out at room temperature.

The present invention will now be elucidated in more detail using the examples which follow.

EXAMPLES

General Methods

Example 1

2-Phase Reaction With (or Without) Phase Transfer Catalyst and Diethyl Ether+Sodium Bicarbonate Solution (Solvent/Water Ratio~1:1)

The polyetheramine (e.g. Jeffamine® T from Huntsman Corp.; 0.015-0.227 mol; dissolved in 200 ml of diethyl ether) and a saturated, filtered aqueous sodium bicarbonate solution (300 ml) are initially charged to a reaction flask. When a phase transfer catalyst is used (at 0.1 to 10% by weight of total amount of substance), it is added to the solution in the reaction flask at room temperature and under agitation. At 0° C. the "glycerol carbonate chloroformate" ((2-oxo-1,3-dioxolan-4-yl)methyl chloroformate) (0.045-0.682 mol; dissolved in 100 ml of diethyl ether) is added at a metered rate in the course of one hour (amount of substance ratio for amine to "glycerol carbonate chloroformate"=1:3) under agitation and the mixture is stirred at room temperature for a further 3.5 hours. Subsequently, the organic phase is separated off in a separation funnel, washed four times with 35 ml of saturated sodium chloride solution each time, dried over sodium sulphate and filtered. The filtrate is concentrated in a rotary evaporator.

Example 2

2-Phase Reaction Without Phase Transfer Catalyst and With Sodium Bicarbonate Solution and THF (Solvent/Water Ratio~1:3)

The polyetheramine (0.06 mol; dissolved in 150 ml of THF) and a saturated, filtered aqueous sodium bicarbonate solution (575 ml) are initially charged to a reaction flask. At 0° C. the "glycerol carbonate chloroformate" ((2-oxo-1,3-dioxolan-4-yl)methyl chloroformate) (0.18 mol; dissolved in 60 ml of THF) is added at a metered rate in the course of one hour (amount of substance ratio for amine to "glycerol carbonate chloroformate"=1:3) under agitation and the mixture is stirred at room temperature for a further 3.5 hours. The organic phase is separated off and the THF is distilled off completely. The residue is taken up in 150 ml of chloroform and washed four times with 35 ml of saturated sodium chloride solution each time, dried over sodium sulphate and filtered. The filtrate is completely concentrated in a rotary evaporator.

Example 3

2-Phase Reaction With Phase Transfer Catalyst and Sodium Bicarbonate Solution and THF (Solvent/Water Ratio~1:1)

The polyetheramine (0.015-0.06 mol; dissolved in 200 ml of THF) and a saturated, filtered aqueous sodium bicarbonate solution (300 ml) are initially charged to a reaction flask. The phase transfer catalyst (at 0.1 to 10% by weight of total amount of substance) is added to the solution in the reaction flask at room temperature and under agitation. At 0° C. the "glycerol carbonate chloroformate" ((2-oxo-1,3-dioxolan-4-yl)methyl chloroformate) (0.0495-0.18 mol; dissolved in 100 ml of THF) is added at a metered rate in the course of one hour (amount of substance ratio for amine to "glycerol carbonate chloroformate"=1:3) under agitation and the mixture is stirred at room temperature for a further 3.5 hours. The organic phase is separated off in a separation funnel and the THF is distilled off completely. The residue was taken up in 150 ml of chloroform and washed four times with 35 ml of saturated sodium chloride solution each time, dried over sodium sulphate and filtered. The filtrate is completely concentrated in a rotary evaporator.

Example 4

1-Phase Reaction in Chloroform with Triethylamine (Similar to WO 2008/142097 A2)

A solution formed from a polyetheramine (0.02-0.06 mol) and triethylamine (dissolved in 50-150 ml of chloroform) is admixed at 0° C. under agitation with a solution formed from 0.0825-0.18 mol of "glycerol carbonate chloroformate" ((2-oxo-1,3-dioxolan-4-yl)methyl chloroformate) in chloroform (20-60 ml). Amount of substance ratio for amine to "glycerol carbonate chloroformate"=1:3; amount of substance used for triethylamine correspondingly 1:1 relative to "glycerol carbonate chloroformate". The solution is stirred at 0° C. for one hour and at 20° C. for a further 20 hours. The solid material is filtered off, the filtrate is washed four times with 35 ml of saturated sodium chloride solution each time, dried over sodium sulphate and filtered. The filtrate is concentrated in a rotary evaporator.

Example 5

1-Phase Reaction in THF with Pyridine

A solution formed from a polyetheramine (0.02-0.091 mol) and pyridine (dissolved in about 200 ml of THF) is admixed at 0° C., under agitation, in the course of 2 hours, with a solution formed from "glycerol carbonate chloroformate" ((2-oxo-1,3-dioxolan-4-yl)methyl chloroformate) (0.06-0.273 mol; dissolved in about 60 ml of THF). Molar ratios for amine to "glycerol carbonate chloroformate"=1:3; amount of substance used for pyridine correspondingly 1:1 relative to "glycerol carbonate chloroformate". The mixture is stirred at room temperature for a further 3 hours. The precipitated solid material is filtered off and the filtrate is completely concentrated in a rotary evaporator. The residue is taken up in 150 ml of chloroform and washed four times with 35 ml of saturated sodium chloride solution each time, dried over sodium sulphate and filtered. The solvent is subsequently distilled off completely.

Specific Methods

Example 6

2-Phase Reaction with Phase Transfer Catalyst and Diethyl Ether+Sodium Bicarbonate Solution (Solvent/Water Ratio=1:1)

Jeffamine® T 403 from Huntsman Corp. (13.20 g; dissolved in 200 ml of diethyl ether) and a saturated, filtered aqueous sodium bicarbonate solution (300 ml) are initially charged to a reaction flask. The phase transfer catalyst tetrabutylammonium hydrogensulphate (5.60 g, corresponds to 10% of total amount of substance) is added to the solution in the reaction flask at room temperature and under agitation. At 0° C. the "glycerol carbonate chloroformate" ((2-oxo-1,3-dioxolan-4-yl)methyl chloroformate) (27.08 g, 90% strength; dissolved in 100 ml of diethyl ether) is added at a metered rate in the course of one hour under agitation and the mixture is stirred at room temperature for a further 3.5 hours. Subsequently, the organic phase is separated off in a separation funnel, washed four times with 35 ml of saturated sodium chloride solution each time, dried over sodium sulphate and filtered. The filtrate is concentrated in a rotary evaporator. Final weight: 19.99 g (yield: 76.4%).

Example 7

2-Phase Reaction Without Phase Transfer Catalyst and With Sodium Bicarbonate Solution and THF (Solvent/Water Ratio=1:3)

Jeffamine® T 403 from Huntsman Corp. (26.40 g; dissolved in 150 ml of THF) and a saturated, filtered sodium bicarbonate solution (575 ml) are initially charged to a reaction flask. At 0° C. the "glycerol carbonate chloroformate" ((2-oxo-1,3-dioxolan-4-yl)methyl chloroformate) (36.11 g; dissolved in 60 ml of THF) is added at a metered rate in the course of one hour under agitation and the mixture is stirred at room temperature for a further 3.5 hours. The organic phase is separated off in a separation funnel and the THF is distilled off completely in a rotary evaporator. The residue is taken up in 150 ml of chloroform and washed four times with 35 ml of saturated sodium chloride solution each time, dried over sodium sulphate and filtered. The filtrate is freed from solvent in a rotary evaporator. Final weight: 17.85 g (yield: 34.1%).

Example 8

2-Phase Reaction Without Phase Transfer Catalyst and With Sodium Bicarbonate Solution and THF on Reverse Order of Addition (Solvent/Water Ratio=1:10)

"Glycerol carbonate chloroformate" ((2-oxo-1,3-dioxolan-4-yl)methyl chloroformate) (36.11 g, 90% strength; dissolved in 60 ml of THF) is initially charged to a reaction flask. At 0° C., under agitation, Jeffamine® T 403 from Huntsman Corp. (26.40 g) dissolved in 575 ml of saturated, filtered aqueous sodium bicarbonate solution in the course of 1.5 hours and stirred at room temperature for a further 3.5 hours. Subsequently, the organic phase is separated off and the THF is distilled off. The residue is taken up in 150 ml of chloroform and washed four times with 35 ml of saturated sodium chloride solution each time, dried over sodium sulphate and filtered. The filtrate is concentrated in a rotary evaporator. Final weight: 7.75 g (yield: 14.8%).

Example 9

2-Phase Reaction With Phase Transfer Catalyst and Sodium Bicarbonate Solution and THF (Solvent/Water Ratio=1:1)

Jeffamine® T 3000 from Huntsman Corp. (75.00 g; dissolved in 200 ml of THF) and a saturated, filtered aqueous sodium bicarbonate solution (300 ml) are initially charged to a reaction flask. The phase transfer catalyst tetrabutylammonium hydrogensulphate (3.65 g, corresponds to 10% of the total amount of substance) is added to the solution in the reaction flask at room temperature and under agitation. At 0° C. the "glycerol carbonate chloroformate" ((2-oxo-1,3-dioxolan-4-yl)methyl chloroformate) (16.55 g, 90% strength+10 excess; dissolved in 100 ml of THF) is metered in during one hour under agitation and stirred at room temperature for a further 3.5 hours. Subsequently, the organic phase is separated off and the THF is distilled off completely. The residue is taken up in 150 ml of chloroform and washed four times with 35 ml of saturated sodium chloride solution each time, dried over sodium sulphate and filtered. The filtrate is concentrated in a rotary evaporator. Final weight: 61.78 g (yield: 72.0%).

Example 10

1-Phase Reaction in Chloroform With Triethylamine (Similar to WO 2008/142097 A2)

A solution of Jeffamine® T 5000 from Huntsman Corp. (100.00 g) and triethylamine (5.00 g), dissolved in 62 ml of chloroform, is admixed at 0° C. and under agitation with the "glycerol carbonate chloroformate" ((2-oxo-1,3-dioxolan-4-yl)methyl chloroformate) (12.04 g; 90% strength dissolved in 43 ml of chloroform). The solution is stirred at 0° C. for one hour and at 20° C. for a further 20 hours. The precipitated solid material is filtered off, the filtrate is washed four times with 35 ml of saturated sodium chloride solution each time, dried over sodium sulphate and filtered. The solvent is completely removed in a rotary evaporator. Final weight: 44.80 g (yield: 41.2%).

The table which follows provides an overview of the experimental results. It is apparent that reaction management in accordance with the present invention provides distinctly higher yields.

TABLE

| Jeffamine ® | Reaction management | Viscosity [mPas] | Yield [%] |
|---|---|---|---|
| T 403 | Et$_2$O/H$_2$O, NaHCO$_3$, PTC*, 2 phases | — | 72.6 |
| | Et$_2$O/H$_2$O, NaHCO$_3$, PTC, 2 phases, 50% chloroformate excess | — | 76.4 |
| | THF/H$_2$O, NaHCO$_3$, no PTC, initially 1 phase, formation of 2 phases at end of reaction | — | 34.1 |
| | THF/H$_2$O, NaHCO$_3$, no PTC, initially 1 phase, formation of 2 phases at end of reaction, reverse order of addition | — | 14.8 |
| T 3000 | Et$_2$O/H$_2$O, NaHCO$_3$, PTC, 2 phases, 10% chloroformate excess | 7134 | 86.9 |
| | THF/H$_2$O, NaHCO$_3$, PTC, 10% chloroformate excess, initially 1 phase, formation of 2 phases at end of reaction | 6800 | 72.0 |
| | THF, pyridine, no PTC, 10% chloroformate excess, 1 phase, the reaction product displayed a strong red to brown discolouration | 9537 | 45.8 |
| T 5000 | Et$_2$O/H$_2$O, NaHCO$_3$, PTC, 2 phases | 3923 | 88.7 |
| | CHCl$_3$, NEt$_3$, no PTC, 1 phase, similar to WO 2008/142097 A2 | 6630 | 41.2 |

*The phase transfer catalyst was tetrabutylammonium hydrogensulphate in each case.

The invention claimed is:

1. A process for preparing cyclocarbonate-functionalized compounds of the general formula (I)

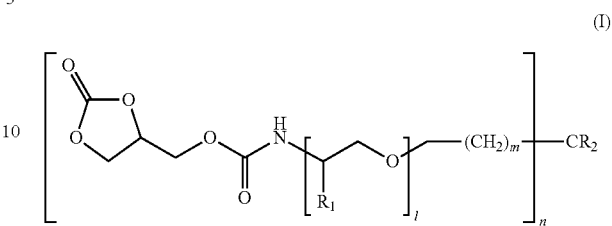

where R$_1$ and R$_2$ in each occurrence are independently selected from hydrogen, methyl and ethyl,
l in each occurrence independently is from 2 to 50,
m in each occurrence independently is 0 or 1, and
n is =3,
subject to the proviso that the sum of all l values in the molecule is from 5 to 100, by reacting a chloroformate of formula (II)

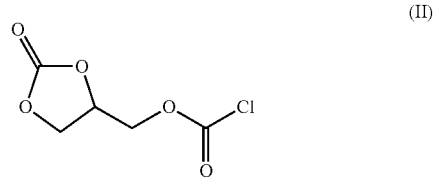 [SMILES: O=C(Cl)OCC1COC(=O)O1]

with a trifunctional amine of the general formula (III)

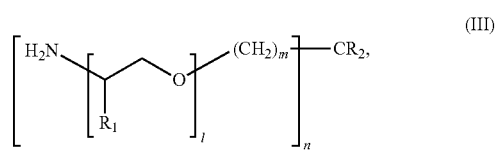

characterized in that
the reaction is carried out in an aqueous/organic two-phase system in the presence of an auxiliary base and of a phase transfer catalyst.

2. The process according to claim 1, characterized in that the organic solvent is selected from tetrahydrofuran, diethyl ether, chloroform, methylene chloride and mixtures thereof.

3. The process according to claim 1, characterized in that the auxiliary base is selected from sodium bicarbonate, pyridine, triethylamine and mixtures thereof.

4. The process according to claim 1, characterized in that the phase transfer catalyst is selected from quaternary ammonium salts.

5. The process according to claim 1, characterized in that 0.1% to 10% by weight of phase transfer catalyst is used, based on the total amount of substance.

6. The process according to claim 1, characterized in that it is carried out at room temperature.

7. The process according to claim 4 wherein the quaternary ammonium salt is tetrabutylammonium hydrogensulphate.

* * * * *